United States Patent

Humphreys, Jr. et al.

[11] Patent Number: 6,086,554
[45] Date of Patent: Jul. 11, 2000

[54] SURGICAL SUCTION/IRRIGATION PROBE ASSEMBLY WITH A ROTATABLE ADAPTOR

[75] Inventors: James E. Humphreys, Jr., Genoa City, Wis.; Donna Allen, Gurnee, Ill.; John N. Johnston, Washington, N.J.

[73] Assignee: Cabot Technology Corporation, Wilmington, Del.

[21] Appl. No.: 09/090,639

[22] Filed: Jun. 4, 1998

[51] Int. Cl.[7] .............................. A61M 1/00; A61M 5/00; F16L 25/00
[52] U.S. Cl. .............................. 604/27; 604/35; 604/264; 285/921
[58] Field of Search ...................... 604/27, 523, 533–535, 604/538, 539, 35, 264; 285/276, 281, 921

[56] References Cited

U.S. PATENT DOCUMENTS

| | | |
|---|---|---|
| 738,503 | 9/1903 | Waters . |
| 1,538,007 | 5/1925 | Schellin . |
| 3,484,121 | 12/1969 | Quinton . |
| 4,248,589 | 2/1981 | Lewis . |
| 4,257,416 | 3/1981 | Prager . |
| 4,451,069 | 5/1984 | Melone . |
| 4,484,769 | 11/1984 | Lacey . |
| 4,580,816 | 4/1986 | Campbell et al. . |
| 4,592,749 | 6/1986 | Ebling et al. . |
| 4,600,221 | 7/1986 | Bimba ........................ 285/91 |
| 4,878,900 | 11/1989 | Sundt ........................ 604/119 |
| 5,049,071 | 9/1991 | Davis et al. . |
| 5,484,402 | 1/1996 | Saravia et al. . |
| 5,551,734 | 9/1996 | Sulzyc et al. ............... 285/174 |
| 5,586,977 | 12/1996 | Dorsey, III . |
| 5,611,576 | 3/1997 | Guala ........................ 285/38 |
| 5,741,084 | 4/1998 | Del Rio et al. ............. 403/349 |

*Primary Examiner*—Mark O. Polutta
*Assistant Examiner*—Michael Hayes
*Attorney, Agent, or Firm*—Austin R. Miller

[57] ABSTRACT

An improved surgical suction/irrigation probe assembly is provided. The unique suction/irrigation probe assembly comprises a handpiece configured to accept a source of irrigation fluid and a source of vacuum or suction. Further, the handpiece provides a means for a surgeon to select either irrigation fluid or suction. Moreover, the handpiece has an outlet region capable of accepting a rotatable adaptor. The assembly further comprises a rotatable adaptor which is capable of being placed into engagement with the outlet region of the handpiece. Further, a shaft and fitting assembly is provided which is snapped into the rotatable adaptor and which shaft is utilized to supply either irrigation fluid or suction to a surgical site.

4 Claims, 4 Drawing Sheets

SURGICAL SUCTION/IRRIGATION PROBE ASSEMBLY WITH A ROTATABLE ADAPTOR

FIELD OF THE INVENTION

This invention relates to an improved surgical suction/irrigation probe assembly More particularly, the invention relates to a suction/irrigation probe assembly comprising: a handpiece having an outlet region capable of accepting a rotatable adaptor; a rotatable shaft adaptor capable of being inserted into said handpiece; and a shaft and fitting assembly which is capable of being inserted into the rotatable adaptor.

DESCRIPTION OF THE PRIOR ART

The use of handheld suction/irrigation probe assemblies is known in the art. Such assemblies typically consist of a handpiece having at one end two separate inlet ports, with one port being connected to a source of irrigation liquid and the second port being connected to a suction source (i.e., vacuum). At the other end of the handpiece is generally a single outlet which is configured to either supply the irrigation fluid or the suction to, for example, a surgical site. The handpiece is generally arranged to provide the surgeon with the ability to choose to supply either irrigation fluid or vacuum to the surgical site by an easily operated means, such as a switch.

Particularly attractive uses of such devices are in the area of endoscopic or laparoscopic surgery. Thus, the devices allow the surgeon to introduce a probe to the surgical site and apply either irrigation fluid or vacuum to the site with relative ease.

One such prior art suction/irrigation probe assembly is detailed in U.S. Pat. No. 5,484,402, which issued to Saravia et al. on Jan. 16, 1996. Saravia et al. provides a suction/irrigation probe assembly consisting of a handheld handpiece having a forward protruding hollow tip for supplying either irrigation liquid or vacuum to a surgical site. The assembly additionally comprises a hand-actuable control for controlling irrigation liquid flow to the tip, and an irrigation said liquid inlet. The assembly further comprises self-contained pumping unit remote from the handpiece to pump irrigation liquid to the handpiece, into the protruding hollow tip, and to the surgical site.

As detailed in Saravia et al., the supply of irrigation fluid and vacuum are provided to a rear end portion of the handpiece by two separate tubes. That is, a first tube supplies irrigation fluid to a first port of the handpiece and a second tube provides a vacuum source to a second port in the handpiece. The handpiece has, at its front end portion, a rigid tubular tip noticeably extending forward from the front end portion of the handpiece for direction toward a surgical site.

The hollow cylindrical tip is mountable removably on the front end portion of the handpiece. An O-ring or the like in an annular groove of a rigid conduit of the handpiece sealingly engages the hollow cylindrical tip fixedly to the front end of the conduit of the handpiece. The subject matter of U.S. Pat. No. 5,484,402 is herein incorporated by reference.

A second such prior art device is described in U.S. Pat. No. 5,586,977, which issued to Dorsey on Dec. 24, 1996. Dorsey discloses a suction/irrigation probe assembly featuring interchangeable probes. Specifically, Dorsey discloses a handpiece which may be connected to an irrigation fluid source and a vacuum source. The handpiece additionally comprises interchangeable probes which may be mounted to the handpiece having a quick disconnect/reconnect mount which permits rapid attachment and rapid removal of probes to and from the handset and additionally provides for the freedom of change in orientation of the probe relative to the handpiece to accommodate variable conditions/requirements of an operative procedure and surgeon preferences. Dorsey discloses a handpiece providing a means for selecting either the irrigation fluid or the vacuum source, as well as a probe assembly for placement into the surgical site. The probe assembly may be attached to the handpiece by use of a specially produced adaptor, or the handpiece may be placed directly onto the handpiece, as described in the patent. The subject matter of U.S. Pat. No. 5,586,977 is herein incorporated by reference.

The search continues in the industry for new, improved suction/irrigation probe assemblies. The present invention provides for a new and improved suction/irrigation probe assembly which will be described below.

SUMMARY OF THE INVENTION

The improved suction/irrigation probe assembly of the present invention generally comprises a handpiece having two separate ports, one port for connection to an irrigation liquid source and a second port for connection to a vacuum or suction source. The handpiece is also provided with an outlet region which is capable of accepting an adaptor. The adaptor is rotatable and capable of being snapped into the handpiece outlet, but remains able to rotate 360° about the axis of the handpiece. The assembly also comprises a shaft and fitting assembly which is capable of being snapped into the rotatable adaptor, wherein the shaft and fitting assembly is then rotatable 360° about the handpiece axis.

The invention allows for the easy connection/disconnection of a variety of shafts, which shafts are then capable of being supplied to a surgical site to supply either irrigation fluid or suction.

As can be appreciated, the invention allows for ease of use of the probe assembly. That is, the invention allows for the user to freely move the handpiece, without twisting/turning the tubes supplying the irrigation liquid and vacuum to the handpiece, by rotating the rotatable adaptor about the axis of the handpiece. Thus, in addition to providing for ease of attaching/detaching a number of shaft assemblies, the assembly is very user friendly.

DETAILED DESCRIPTION OF THE INVENTION

The improved suction/irrigation probe assembly of the present invention generally comprises a handpiece having two separate ports, one port for connection to an irrigation liquid source and a second port for connection to a vacuum or suction source. A means for selecting either irrigation liquid or vacuum is provided, for example, a switch or similar device. The handpiece is also provided with an outlet region which is capable of accepting the rotatable adaptor. The rotatable adaptor is capable of being snapped into the handpiece outlet, but remains able to rotate 360° about the axis of the handpiece. The assembly also comprises a shaft and fitting assembly which is capable of being snapped into the rotatable adaptor, wherein the shaft and fitting assembly is then rotatable 360° about the handpiece axis. By operating the switch or similar device, the surgeon can selectively supply either irrigation fluid or vacuum to a surgical site.

The invention allows for the easy connection/disconnection of a variety of shafts, which shafts are then capable of being supplied to a surgical site to supply either irrigation fluid or suction.

A better understanding of the invention may be had with reference to the Figures.

Figure 1:
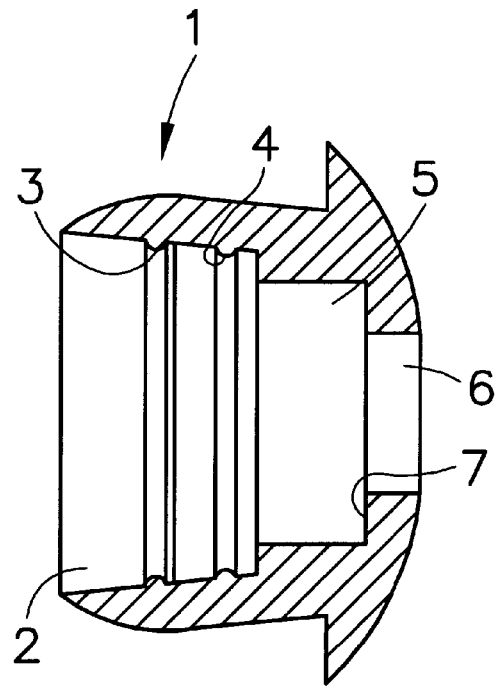
FIG. 1 is a schematic cross-section of a portion of a handpiece showing an outlet portion capable of accepting a rotatable adaptor according to the present invention.

The handpiece of the present invention has an outlet region 1, detailed in FIG. 1. The handpiece outlet region 1 includes a counterbore region 2 that extends into the body of the handpiece, with the diameter of the counterbore region decreasing slightly as it extends into the handpiece. The counterbore region 2 is shaped to receive the shaft adaptor 10, described below. A first radial rib 3 is provided on the inside surface of a larger diameter portion of the counterbore region 2. Somewhat farther into the body of the handpiece is a second radial rib 4 located on a slightly smaller diameter portion of the counterbore region 2. A second counterbore region 5 extends farther into the handpiece's body from which a flow passage 6 extends for fluid flow to/from the source of irrigation fluid and vacuum.

Figure 2A:
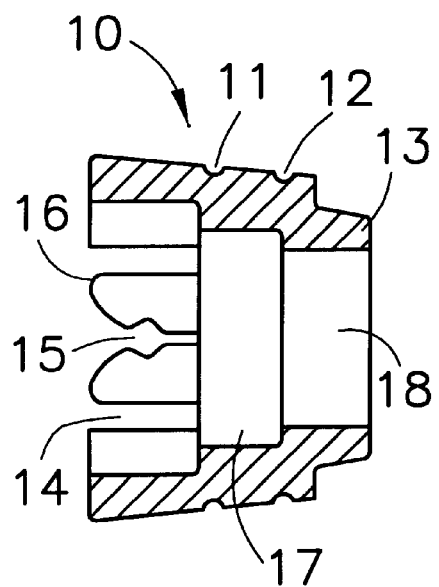
FIG. 2A is a schematic cross-section showing a rotatable adaptor according to the present invention.
Figure 2B:
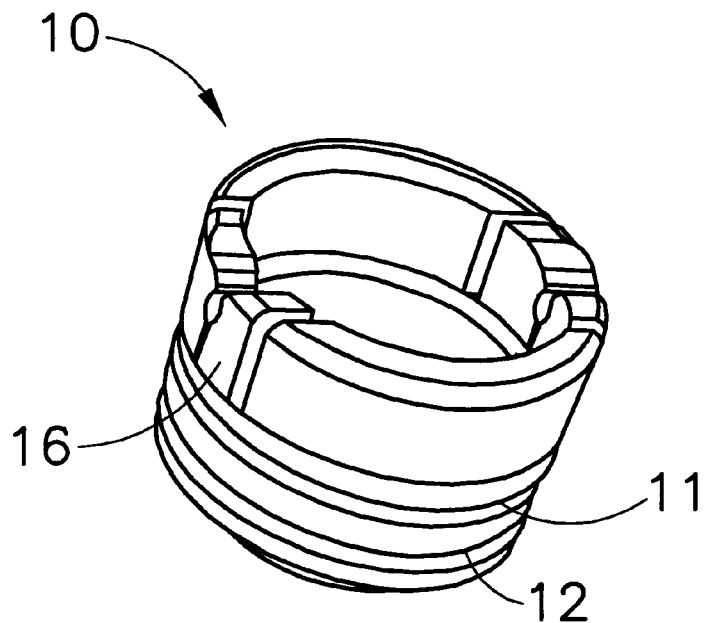
FIG. 2B is a perspective view of the rotatable adaptor of FIG. 2A.

The rotatable adaptor 10 of the invention is illustrated in FIGS. 2A and 2B. The rotatable adaptor 10 is shaped for insertion into the counterbore region 2 of the handpiece outlet 1. The outer surface of the rotatable adaptor 10 includes a first radial groove 11 that extends around the circumference of the rotatable adaptor and a second radial groove 12 adjacent the first radial groove 11 that also extends about the circumference of the rotatable adaptor 10.

When the rotatable adaptor 10 is installed into the outlet region 1 of the handpiece, radial rib 3 of the outlet region 1 engages radial groove 11 of the rotatable adaptor 10 and radial rib 4 of the outlet region 1 engages radial groove 12 of the rotatable adaptor 10. When the rotatable adaptor 10 is placed into engagement with the outlet region 1 of the handpiece, such engagement firmly locks the rotatable adaptor 10 into the handpiece, yet permits 360° rotation of the rotatable adaptor 10 with respect to the handpiece axis.

Further, when the rotatable adaptor 10 is inserted into the outlet region 1 of the handpiece, the end portion 13 of the rotatable adaptor 10 extends into the second counterbore region 5 of the outlet region 1 of the handpiece. In a preferred embodiment, an O-ring is positioned between the end portion 13 of the rotatable adaptor 10 and the portion of the second counterbore region 5 of the outlet region 1 of the handpiece, indicated by the numeral "7". The use of such an O-ring seal, or similar sealing means, may be desirable to provide a better, fluid-tight seal between the handpiece and the rotatable adaptor 10.

The rotatable adaptor 10 additionally comprises a first counterbore region 14. Further, at least two recesses 15 are provided for the engagement of the shaft and fitting assembly, described below. Each recess 15 is flanked by two wall portions 16 that can flex for snap-in engagement of the shaft and fitting assembly, described below. The rotatable adaptor 10 additionally comprises a second counterbore region 17 of smaller diameter than the first counterbore region 14 and, additionally, comprises a flow opening 18.

Figure 3:
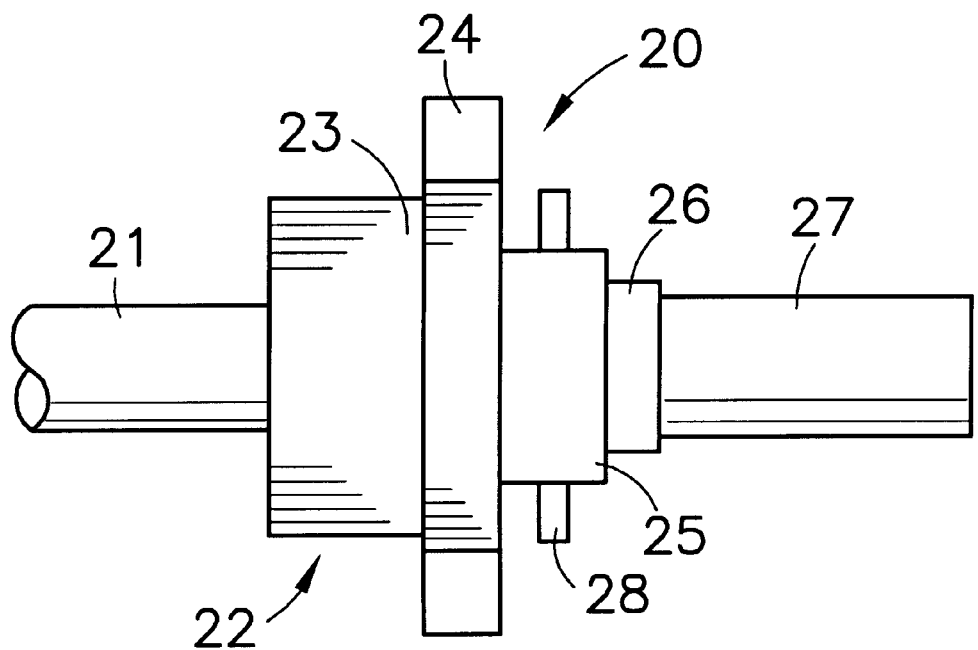
FIG. 3 is a schematic of a shaft and fitting assembly according to the present invention.
Figure 4:
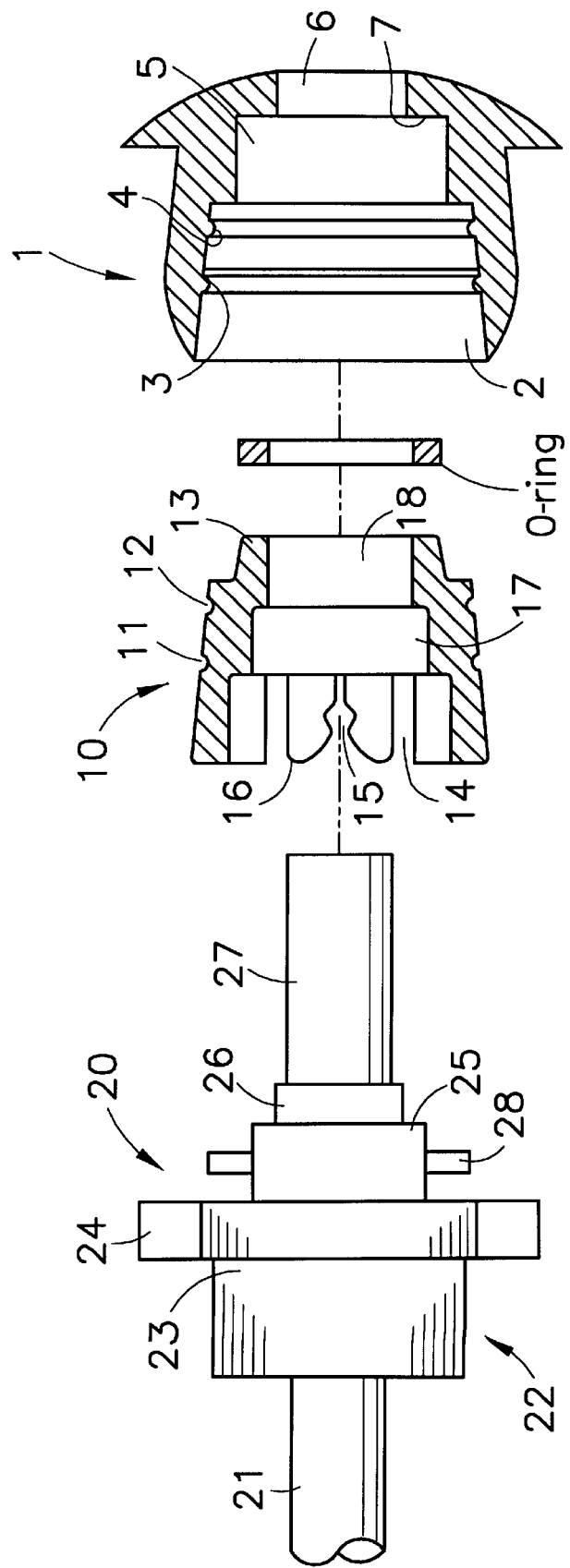
FIG. 4 is a schematic drawing showing the outlet portion of the handpiece, the rotatable adaptor, and the shaft and fitting assembly, just prior to assembly.
Figure 5:
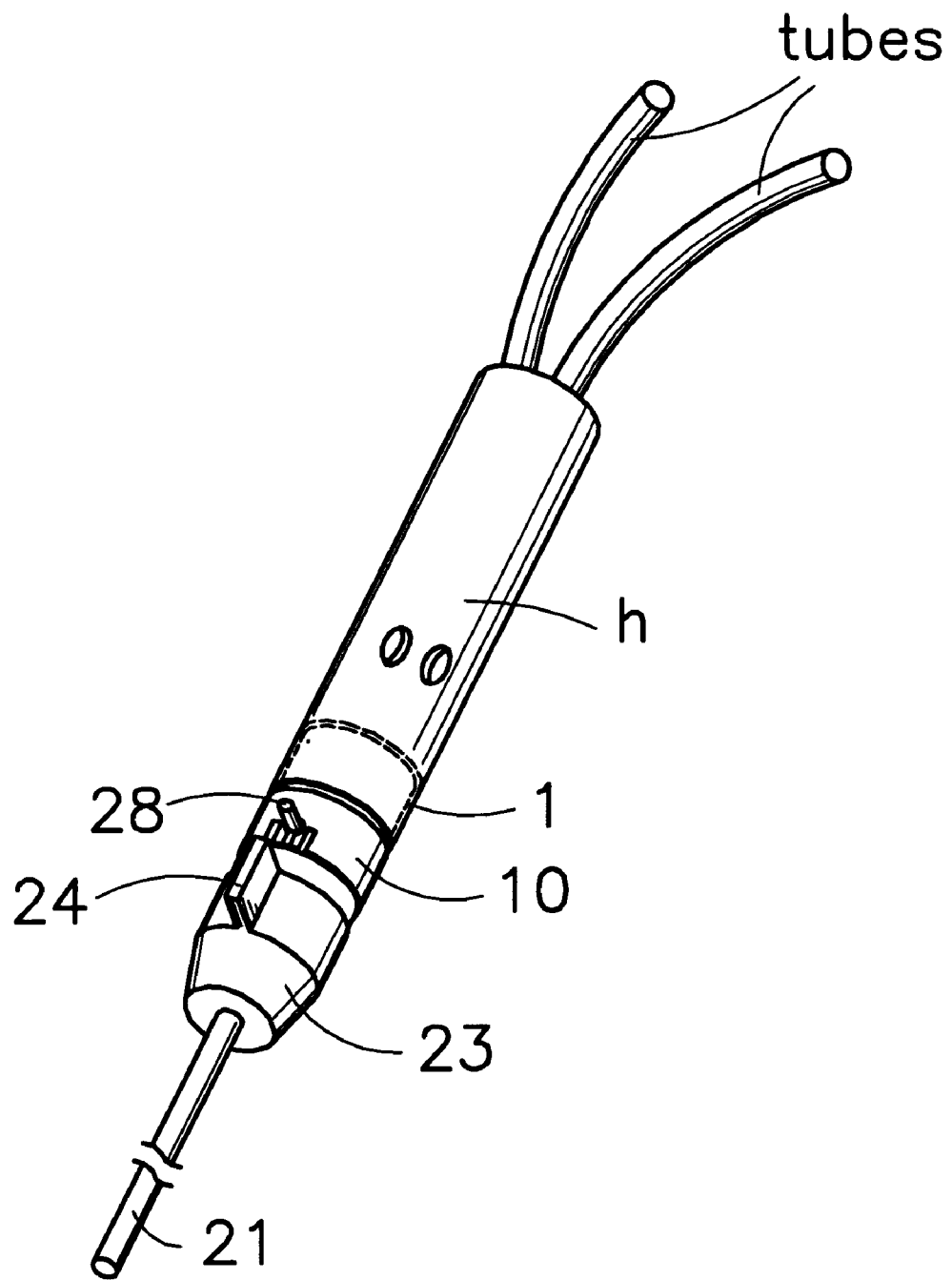
FIG. 5 is a perspective veiw of the probe assembly.

The invention finally comprises the shaft and fitting assembly 20, shown in FIG. 3. As shown in FIG. 3, the shaft and fitting assembly 20 includes a tubular shaft 21, which is preferably made of stainless steel, that is fixed into a fitting 22 (preferably a plastic fitting). The fitting has a knob 23 at a first side for rotation of the shaft 21 with respect to the handpiece. Two opposed ears or protrusions 24 may be supplied to assist such rotation of the shaft 21. Immediately adjacent the fitting 22 is a first shoulder 25, a second shoulder 26, and an extension 27. At least two opposed protrusions 28, each preferably having a cylindrical shape, extend outwardly from the first shoulder 25.

As can be seen, when the shaft and fitting assembly 20 is installed into the rotatable adaptor 10, the first shoulder 25 extends into the counterbore 14 of the rotatable adaptor 10 and the fitting protrusions 28 are snapped into the recesses 15 of the rotatable adaptor 10. The shaft and fitting assembly's second shoulder 26 extends into the rotatable adaptor's second counterbore region 17 and the fitting's extension 27 extends into the rotatable adaptor's opening 18.

Rotation of the shaft fitting's knob portion 23 and ears 24 causes rotation of the rotatable adaptor 10 by engagement between the fitting protrusions 28 and the adaptor recesses 15. The O-ring, which may be positioned in the second counterbore region 5 of the handpiece outlet region 1, as discussed above, may provide a seal between the fitting 10 and the handpiece.

Thus, it will now be appreciated that the present invention provides a significant improvement over the prior art. The invention provides a versatile surgical suction/irrigation probe assembly which allows the surgeon the ability to freely move the shaft portion of the assembly about a surgical site, while not being hampered by twisting and tangling of the tubes supplying the irrigation fluid and vacuum to the handpiece portion of the probe assembly. Additionally, the invention provides for the easy connection/disconnection of a variety of shafts.

The above description provides a detailed explanation of representative and preferred embodiments of this invention. The skilled artisan will now understand that numerous changes may be made to the present invention without departing from the scope of the invention which is set forth in the following claims.

What is claimed is:

1. A suction/irrigation probe assembly comprising:
    a handpiece having an outlet region capable of accepting a rotatable adaptor;
    a rotatable adaptor placed into selective engagement with said outlet region of said handpiece, said adaptor having resilient wall portions defining at least two opposed recesses; and
    a shaft assembly selectively engaging said adaptor for rotation therewith with respect to said handpiece, said shaft assembly being provided with at least two opposed protrusions for snap-in engagement within said recesses defined by said resilient wall portions of said adaptor.

2. The probe assembly of claim 1, further comprising an O-ring located between said rotatable adaptor and said outlet region of said handpiece.

3. The probe assembly of claim 1, wherein said outlet region of said handpiece comprises a counterbore region having at least two radial ribs, and said rotatable adaptor comprises at least two radial grooves for engagement by said radial ribs to secure said rotatable adaptor into said outlet region of said handpiece.

4. The probe assembly of claim 3, wherein said counterbore region reduces in diameter between said radial ribs such that said radial ribs are of different diameters.

* * * * *